United States Patent
Bosman et al.

(10) Patent No.: US 7,622,131 B2
(45) Date of Patent: Nov. 24, 2009

(54) SILOXANE POLYMERS WITH QUADRUPLE HYDROGEN BONDING UNITS

(75) Inventors: Anton Willem Bosman, Eindhoven (NL); Hendricus Marie Janssen, Eindhoven (NL); Gaby Maria Leonarda Van Gemert, Roermond (NL); Ronny Mathieu Versteegen, Horst (NL); Egbert Willem Meijer, Waalre (NL); Rintje Pieter Sijbesma, s-Hertogenbosch (NL)

(73) Assignee: Suprapolix B.V., Eindhoven (NL)

( * ) Notice: Subject to any disclaimer, the term of this patent is extended or adjusted under 35 U.S.C. 154(b) by 471 days.

(21) Appl. No.: 11/148,552

(22) Filed: Jun. 9, 2005

(65) Prior Publication Data
US 2006/0018856 A1 Jan. 26, 2006

Related U.S. Application Data

(63) Continuation of application No. PCT/NL03/00870, filed on Dec. 9, 2003.
(60) Provisional application No. 60/431,712, filed on Dec. 9, 2002.

(30) Foreign Application Priority Data

Dec. 9, 2002 (EP) .................. 02080202

(51) Int. Cl.
*A61K 8/89* (2006.01)
*A61K 31/74* (2006.01)
*A61Q 15/00* (2006.01)
*C08G 77/00* (2006.01)
*C08G 77/26* (2006.01)
*C08G 77/388* (2006.01)

(52) U.S. Cl. ............ 424/401; 424/65; 424/70.12; 424/78.02; 528/10

(58) Field of Classification Search ............ None
See application file for complete search history.

(56) References Cited

U.S. PATENT DOCUMENTS

| 5,500,209 | A | 3/1996 | Ross et al. |
|---|---|---|---|
| 5,874,069 | A | 2/1999 | Mendolia et al. |
| 5,919,441 | A | 7/1999 | Mendolia et al. |
| 6,320,018 | B1 | 11/2001 | Sijbesma et al. |
| 6,353,076 | B1 | 3/2002 | Barr et al. |
| 2001/0053377 | A1 | 12/2001 | Mondet et al. |
| 2003/0092838 | A1 | 5/2003 | Fomperie et al. |
| 2004/0161394 | A1 | 8/2004 | Mougin et al. |

FOREIGN PATENT DOCUMENTS

| EP | 1 310 533 A2 | 5/2003 |
|---|---|---|
| WO | WO 98/14505 A1 | 4/1998 |

OTHER PUBLICATIONS

Sijbesma et al., "Reversible Polymers formed from Self-Complementary Monomers Using Quadruple Hydrogen Bonding", Nov. 28, 1997, Science, vol. 278, pp. 1601-1604, USA.
Folmer et al., "Supramolecular Polymer Materials: Chain Extension of Telechelic Polymers Using a Reactive Hydrogen-Bonding Synthon", Adv. Materials, 2000, vol. 12, No. 12, pp. 874-878, Germany.
Hirschberg et al., Supramolecular Polymers from Linear Telechelic Siloxane with Quadruple-Hydrogen-Bonded Units, Macromolecules, 1999, vol. 32, pp. 2696-2705, USA.

*Primary Examiner*—Johann R Richter
*Assistant Examiner*—Christopher R Lea
(74) *Attorney, Agent, or Firm*—Gilberto M. Villacorta; Sunit Talapatra; Foley & Lardner LLP

(57) ABSTRACT

The invention relates to the synthesis of siloxane polymers containing self-complementary quadruple hydrogen bonding groups (4H-units). The resulting polymers show unique new characteristics that result from the reversible, physical interactions between the polysiloxane chains that are based on the (supramolecular) interactions between the 4H-units. The polysiloxanes in this invention show unprecedented bulk material properties and are used as gelling agents for silicone fluids. The resulting gels are clear and display good material properties, while having unparalleled high silicone fluid contents.

13 Claims, No Drawings

SILOXANE POLYMERS WITH QUADRUPLE HYDROGEN BONDING UNITS

CROSS REFERENCE TO RELATED APPLICATIONS

This application is a continuation of international application number PCT/NL03/00870, filed Dec. 9, 2003, which claims domestic priority to U.S. provisional application No. 60/431,712, filed Dec. 9, 2002, and foreign priority to European patent application number 02080202.1, filed Dec. 9, 2002, the disclosures of which are hereby incorporated in their entirety by reference.

FIELD OF THE INVENTION

The invention relates to the synthesis of siloxane polymers containing self-complementary quadruple hydrogen bonding groups (4H-units). The resulting polymers show unique new characteristics that result from the reversible, physical interactions between the polysiloxane chains that are based on the (supramolecular) interactions between the 4H-units. The polysiloxanes in this invention show unprecedented bulk material properties and are used as gelling agents for silicone fluids. The resulting gels are clear and display good material properties, while having unparalleled high silicone fluid contents.

BACKGROUND AND DESCRIPTION OF THE INVENTION

This invention relates to siloxane-based polymers (polysiloxanes) with different architectures and molecular weights that contain units that are capable of forming strong H-bridges with each other leading to reversible physical interactions between different polymer chains in bulk and in solution. The supramolecular H-bridge interactions are specific as they exist between self-complementary units containing 4 hydrogen bonds in a row (i.e. 4H-units), and the action of these 4H-units results in superior material characteristics. For details on the 4H-unit, see Sijbesma et al. WO 98/14505; Science, 278, 1601.

Although several telechelic polymers have been modified with 4H-units before (Folmer, B. J. B. et al., Adv. Mater. 2000, Vol. 12, 874), only one example of a low molecular weight telechelic polysiloxane modified with 4H-units has been described previously in patent WO 98/14505; (later published in Hirschberg et al., Macromolecules 1999, Vol. 32, 2696). Major drawback of the polysiloxane polymer described in this patent is the elaborate procedure to couple the 4H-unit to the polymer in which a protection/deprotection procedure is necessary. Moreover, the resulting polymer contains only two 4H-units on both ends and has a limited molecular weight.

This invention is further related to the use of polysiloxanes functionalized with 4H-units as gelling agents for silicone fluids (for example, volatile or non-volatile silicone liquids). The resulting gels are clear and contain small amounts of gelling agent; their physical characteristics can be fine-tuned by selecting the right 4H-unit modified polysiloxane or by combining a set of such polysiloxanes. Moreover, the prepared gels can be used in personal care applications, for example as carriers for cosmetic or dermatological active ingredients in order to obtain cosmetic or dermatological active compositions. Particular embodiments of the present invention are skin-care compositions such as deodorant and antiperspirant compositions, sun protection compositions and hair-care compositions.

Because gels based on volatile silicones (cyclomethicones) reduce tackiness and stickiness of cosmetic or dermatological formulations, there has been an increasing need for cosmetic or dermatological compositions with high cyclomethicone content. In U.S. Pat. No. 5,500,209 this has been achieved by using polyamides as gelling agent, however only limited amounts of cyclomethicones can be added because of the immiscibility with the polyamide and the high crystallinity of the polyamide.

In order to improve the miscibility with silicone fluids, polyamides containing polysiloxane blocks have been prepared, as described in U.S. Pat. No. 5,874,069, and U.S. Pat. No. 6,353,076B1. Drawbacks of these inventions are the poor gelling characteristics compared to the gellants disclosed here, because of the relatively weak interactions between different polyamides. As a consequence, high molecular weight polymers have to be used to obtain stable gels, the amount of gelling agent has to be high, and non-silicone viscosity builders have to be added.

In U.S. Pat. No. 5,919,441 main-chain siloxane urea polymers are used containing polysiloxane-segments and polar segments with urea, urethane, amide and thiourea groups or combinations of these groups. Drawbacks of this invention are the high molecular weights of the used polymers, hampering good processability of the material, and the presence of a relatively high amount of non-siloxane, cyclomethicone immiscible groups, thereby reducing the amount of cyclomethicone that can be thickened by the gelling agent. Moreover, a major drawback of this invention is the relative weakness of the secondary interactions between different polysiloxanes, as this requires high amounts of thickener to obtain stable gels and additional viscosity builders in the cosmetic applications.

This invention describes the unprecedented synthesis of polysiloxanes containing one or more 4H-units capable of forming strong, but reversible physical interactions with each other. Due to the presence of the 4H-units the polysiloxanes display unique new material properties in bulk and in solution. In a particular embodiment of this invention, the effective gelling behavior of these modified polysiloxanes is used to thicken volatile silicone solvents, creating transparent gels with low or very low thickener content and excellent material properties. The resulting thickened volatile silicones are ideal carriers for cosmetic or dermatological active ingredients and therefore have several cosmetic or dermatological applications.

Description of Siloxane Polymers Containing Self-Complementary Quadruple Hydrogen Groups The polysiloxanes described in this invention preferably correspond to the following general formulae (3a) or (3b):

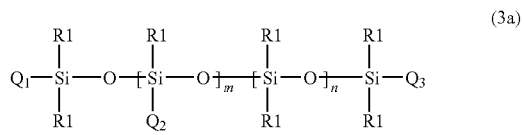

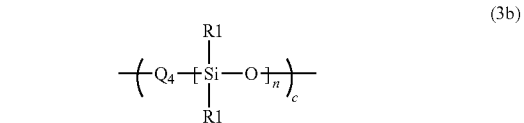

in which the radicals R1, that may be identical or different, are selected from substituted and unsubstituted monovalent nonaromatic ethylenically free $C_1$-$C_{20}$ hydrocarbon radicals, or are selected from aromatic radicals, $Q_1$ and $Q_2$ and $Q_3$ are equal and denote one or more structural elements that are capable of forming at least four hydrogen bridges (also referred to as 4H-unit) and that are attached via a linker through a silicon-carbon bond to the polymer, or $Q_1$ and $Q_3$ are equal and denote one or more 4H-units attached via a linker through a silicon-carbon bond to the polymer and $Q_2$ is defined as R1, or $Q_1$ denotes one or more 4H-units attached via a linker through a silicon-carbon bond to the polymer and $Q_2$ and $Q_3$ are defined as R1, or $Q_2$ denotes one or more 4H-units attached via a linker through a silicon-carbon bond to the polymer and $Q_1$ and $Q_3$ are equal and are defined as R1, $Q_4$ is a 4H-unit having two linkers that are attached through a silicon-carbon bond to the polymer chain, and m, n and c are integers such that the mean molecular weight of the polysiloxane ranges from 500 to 250000.

R1 is preferably an alkyl radical, more preferably a $C_1$-$C_{20}$ alkyl radical and especially a methyl, ethyl, propyl, isopropyl, butyl, pentyl, hexyl, octyl, decyl, dodecyl or an octadecyl radical, a cycloalkyl radical, more preferably a $C_1$-$C_{20}$ cycloalkyl radical, even more preferably a $C_1$-$C_{10}$ cycloalkyl radical and in particular a cyclohexyl radical, an aryl radical, more preferably a $C_1$-$C_{20}$ aryl radical, even more preferably a $C_1$-$C_{10}$ aryl radical and especially a phenyl or a naphtyl, an arylalkyl radical, more preferably a $C_1$-$C_{20}$ arylalkyl radical, even more preferably a $C_1$-$C_{10}$ arylalkyl radical and especially a benzyl, phenylethyl, tolyl or a xylyl radical. Most preferably R1 is a methyl radical.

In general, the structural element (4H-unit) that is capable of forming four hydrogen bridges preferably has the general form of (1) or (2):

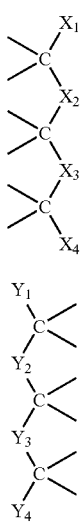

(1)

(2)

In all general forms shown above, the C—$X_i$ and C—$Y_i$ linkages each represent a single or double bond, and $X_1 \ldots X_4$ represent donors or acceptors that form hydrogen bridges with the H-bridge-forming unit containing a corresponding structural element (2) linked to them, with $X_i$ representing a donor and $Y_i$ an acceptor or vice versa. Properties of the structural element having general forms (1) or (2) are disclosed in U.S. Pat. No. 6,320,018 which for the US practice is incorporated herein by reference.

The 4H-units contain four donors or acceptors, are self-complementary and in pairs form four hydrogen bridges with one another. Preferably, the 4H-unit has two successive donors, followed by two successive acceptors, preferably structural elements according to the general form (1), in which $X_1$ and $X_2$ both represent a donor or an acceptor, respectively, and $X_3$ and $X_4$ both an acceptor or a donor, respectively. According to the invention, the donors and acceptors are preferably O, S, and/or N atoms.

Molecules that can be used to construct the structural element $Q_n$ (see formulae (3a) and (3b)) are nitrogen containing compounds that are reacted with isocyanates or thioisocyanates, or that are activated and reacted with primary amines, to obtain a urea moiety that is part of the quadruple hydrogen bonding site. The nitrogen containing compound is preferably an isocytosine derivative (i.e. a 2-amino-4-thymidone or otherwise named 2-amino4-hydroxy pyrimidine derivative) or a triazine derivative, or a tautomer of these derivatives. More preferably, the nitrogen containing compound is an isocytosine having an alkyl, alkyl carboxylic acid or oligoethylene glycol in the 6-position, most preferably a methyl or ethylhexyl group, or an isocytosine with a methyl in the 6-position and a 2-hydroxy ethyl group in the 5-position. The isocyanates or the thioisocyanates can be monofunctional isocyanates or monofunctional thioisocyanates or bifuntional diisocyanates or bifunctional thioisocyanates. Preferably, these compounds are diisocyanates or dithioisocyanates, in particular diisocyanates. Examples of suitable diisocyanates that can be used in this invention are:

1,4-diisocyanato-4-methyl-pentane,
1,6-diisocyanato-2,2,4-trimethylhexane,
1,6-diisocyanato-2,4,4-trimethylhexane,
1,5-diisocyanato-5-methylhexane,
3(4)-isocyanatomethyl-1-methylcyclohexyl isocyanate,
1,6-diisocyanato-6-methyl-heptane,
1,5-diisocyanato-2,2,5-trimethylhexane,
1,7-diisocyanato-3,7-dimethyloctane,
1-isocyanato-1-methyl-4-(4-isocyanatobut-2-yl)-cyclohexane,
1-isocyanato-1,2,2-trimethyl-3-(2-isocyanato-ethyl)-cyclopentane,
1-isocyanato-1,4-dimethyl-4-isocyanatomethyl-cyclohexane,
1-isocyanato-1,3-dimethyl-3-isocyanatomethyl-cyclohexane,
1-isocyanatol-n-butyl-3-(4-isocyanatobut-1-yl)-cyclopentane.
1-isocyanato-1,2-dimethyl-3-ethyl-3-isocyanatomethyl-cyclopentane,
3(4)-isocyanatomethyl-1-methylcyclohexyl isocyanate (IMCI),
toluene diisocyanate (TDI),
methylene diphenyl diisocyanate (MDI),
methylene dicyclohexane 4,4-diisocyanate,
isophorone diisocyanate (IPDI), hexane diisocyanate (HDI).

Examples of suitable thioisocyanates are the dithioisocyanate derivatives of the compounds exemplified above for suitable dithiocyanates.

Preferably, the diisocyanate is IPDI, HDI, MDI, TDI or methylene dicyclohexane 4,4-diisocyanate and their thioisocyanate counterparts. According to the invention, however, the diisocyanates are more preferably used than dithioisocyanates.

A particularly suitable structural element $Q_n$ according to the invention is the element shown below having the general formulae (4), and tautomers thereof:

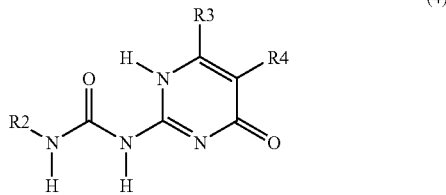

(4)

wherein R2, R3 or R4 represent a linking moiety through which the 4H-unit according to formula (4) is bonded to the polysiloxane with the other R groups representing a random side chain or are hydrogen atoms. More preferably, R2 is the linking moiety, whereas R3 and R4 are a random side chain or are hydrogen atoms. Most preferably, R3 is a random side chain and R4 a hydrogen atom, wherein the random side chain is an alkyl or oligoethylene glycol group, most preferably methyl or ethylhexyl. In another embodiment of this invention, R2 and R3, or R2 and R4 represent linking moieties through which the 4H-unit according to formula (4) is bonded to the polysiloxane with the other R group representing a random side chain or a hydrogen atom. More preferably, R2 and R4 are the linking moieties, whereas R3 is a random side chain or a hydrogen atom. Most preferably, the random side chain is an alkyl or oligoethylene glycol group, most preferably methyl or ethylhexyl.

The linking moieties may be all kinds of shorter or longer chains, for example saturated or unsaturated, branched, cyclic or linear alkyl chains, oligosiloxane chains, oligoester chains, oligoether chains and any chain of atoms used in traditional polymer chemistry, whether or not substituted with functional groups such as esters, ethers, ureas or urethanes. Preferably, the linking moiety is a $C_1$-$C_{20}$ straight chain or branched alkylene, arylene, alkarylene or arylalkylene group, more preferably a $C_2$-$C_{10}$ straight chain or branched alkylene, arylene, alkarylene or arylalkylene group, wherein the alkylene, arylene, alkarylene or arylalkylene group may be substituted with other groups or may contain cyclic groups as substituent or in the main chain. Examples of such groups are methylene, ethylene, propylene, tetramethylene, pentamethylene, hexamethylene heptamethylene, octamethylene, nonamethylene, 1,6-bis(ethylene)cyclohexane, 1,6-bismethylene benzene, etc. The alkylene, arylene, alkarylene or arylalkylene groups may be interrupted by heteroatoms, in particular heteroatoms selected from the group of oxygen, nitrogen, and sulphur.

Examples of the structural element $Q_n$ are elements according to formula (4) in which R2 is a propylene group, R3 is a methyl and R4 is a proton, or in which R2 is [1,3,3-trimethyl-5-(3-propyl-ureido)-cyclohexyl]-methyl, R3 is methyl and R4 is a proton, or in which R2 is 3-(3-propyl-ureido-methyl)-3,5,5-trimethyl-cyclohexyl, R3 is methyl and R4 is a proton, or in which R2 is 3-(hexyloxycarbonylamino-methyl)-3,5,5-trimethyl-cyclohexyl, R3 is methyl and R4 is [3-(hexyloxycarbonylamino-methyl)-3,5,5-trimethyl-cyclohexyl]-carbamic acid ethyl ester.

The number of repeat units m, see formula (3a), ranges from 0 to 700, more prefentially from 0 to 50, even more prefentially from 0 to 10.

The number of repeat units n, see formulae (3a) and (3b), ranges from 0 to 700, more prefentially from 5 to 400.

According to the present invention the polysiloxanes modified with 4H-units are obtained in five different ways: (i) polysiloxanes containing functional end groups are reacted with a reactive synthon containing the 4H-unit or with a reactive synthon thus creating the 4H-unit, or (ii) polysiloxanes containing pendant functional groups along the polymer chain in a comb-branch fashion are reacted with a reactive synthon containing the 4H-unit or with a reactive synthon thus creating the 4H-unit, or (iii) polysiloxanes containing functional end-groups and pendant functional groups along the polymer chain in a comb-branch fashion are reacted with a reactive synthon containing the 4H-unit or with a reactive synthon thus creating the 4H-unit, or (iv) by ring opening polymerization of a cyclic siloxane monomer in the presence of a functional terminator containing two or more 4H-units, or (v) by co-polymerization of cyclic siloxane monomers with cyclic siloxane monomers that are functionalized with one or more 4H-units.

In a preferred embodiment of this invention the functional pendant groups and end-groups in the polysiloxane are hydride, aminopropyl, aminoethylaminopropyl, aminoethylaminoisobutyl, alkanol, hexanol, an aliphatic diol, hydroxy terminated poly(ethyleneglycol), hydroxy terminated poly(ethylene-co-propylene) glycol, or hydroxy terminated oligocaprolacton. When the polysiloxane contains hydride functions, the 4H-unit according to formula (4) is preferably defined with R2 is allyl, R3 is methyl, R4 is proton. When the polysiloxane contains amino and/or alcohol functions, the 4H-unit according to formula (4) is defined with R2 forms an imidazole-ring with the nitrogen attached to R2, R3 is methyl, R4 is proton, or R2 is methyl(3-isocyanato-3,5,5-trimethyl-cyclohexyl) or 1,3,3-trimethyl-5-(isocyanatomethyl)-cyclohexyl, and R3 is methyl, R4 is proton.

Examples of polysiloxanes with functional groups include the following (1) to (3) pre-polymers:

(1) telechelic polysiloxanes: specific examples include, hydride functional series sold as DMS-H21, DMS-H25, DMS-H31 (Gelest); amino-functional series sold as DMS-A12, DMS-A15, DMS-A21, DMS-A32 (Gelest), or X-22-161B, KF-8012 (Shin-Etsu); alcohol functional series KF-6001, KF-6002, KF-6003, X-22-176-DX (Shin-Etsu), or TEGO IS 4181, TEGO IS 4480 P (Goldschmidt).

(2) pendant functional polysiloxanes: specific examples include, hydride functional series sold as HMS-064, HMS-071, HES-992, HAM-303 (Gelest); amino-functional series sold as AMS-152, AMS-162 (Gelest), or KF-864, KF-868 (Shin-Etsu), or amidomethicones sold under several trade names by Shin-Etsu, Dow Corning Corporation, GE-Bayer Silicones, Wacker-Chemie, or hydroxyl-functional dimethicone copolyols sold under several trade names by Shin-Etsu, Dow Corning Corporation, GE-Bayer Silicones.

(3) pendant and end group functional polysiloxanes: specific examples include, hydride functional series sold as HDP-111, HPM-502 (Gelest); amino- and alkoxy-functional series sold as KF857, KF-862 (Shin-Etsu).

In another embodiment of this invention the previous mentioned polysiloxanes modified with 4H-units are used as thickeners of silicone fluids. The combination of the high solubility of the polysiloxanes in silicones and the strong interchain interactions caused by the presence of the 4H-units, result in the formation of gels with high silicone contents up to about 98%. Examples of silicone fluids that can be gelled are linear siloxanes known as dimethicones, linear siloxanes containing an aromatic substitution such as phenyltrimethicone and cyclic siloxanes having 4-6 members in a ring, optionally substituted by $C_1$-$C_6$ alkyl or phenyl, particularly cyclic dimethyl siloxanes such as cyclomethicones. Mixtures of these silicone fluids may also be used.

The thickeners described in the present invention are fully miscible with silicones solvents such as cyclomethicone due to their high silicone content and relatively low molecular weight. Gellation of silicone solvents takes place by an amount of thickener in between 1-40% by weight, more particularly 1-25% by weight, most particularly 2-15% by weight.

Clear gels are obtained by heating the polysiloxane modified with the 4H-unit in the presence of silicone fluid at a temperature between 25 and 130° C., followed by cooling to room temperature. Dependent on the nature and the amount of the polysiloxane modified with the 4H-unit that is used, the gels are structurally stable from 0°-60° C.

The rigidity of the gels is strongly dependent on the polysiloxane gellant that is used. Increasing the number of 4H-units per chain leads to a more rigid gel, while increasing the molecular weight of the polysiloxane makes the gel stronger. Consequently, a complete range of gels can be obtained, from soft to firm, by mixing different types of gelling agents in different amounts of silicone fluid, and in different kinds of silicone fluids.

Personal care applications such as cosmetic or dermatological compositions can be formulated by adding at least one cosmetic or dermatological active ingredient in a sufficient amount to the silicone fluid and the polysiloxane thickener in such a way that a composition is obtained with the right cosmetic or dermatological activity and the right viscosity. Optionally, surface-active agents, emollients, and/or solvents for the cosmetically active material are added to the composition. Moreover, the composition can have different physical appearances depending on amount and nature of the polysiloxane thickeners described in this invention, for example: stick, gel, cream, mousse or solution.

The reversible nature of the 4H-units allows easy application of the cosmetic or dermatological composition by the user since heating and/or diluting of the composition results in a dramatic lowering of the viscosity and consequently a composition that is much easier to process. These processing advantages together with the specific beneficial characteristics of polysiloxanes in cosmetic products that are well known in the art (i.e. reduced stickiness and tackiness), result in unique applications in hair care products, make-up products, skin care products, antiperspirants, deodorants, all dependent on the specific cosmetic active ingredient added.

EXAMPLES

The invention will now be clarified with examples, without however being limited thereby.

The following examples describe:
(i) the synthesis of building blocks; reactive synthons that contain the 4H-unit or that give the 4H-unit after reaction with functional polysiloxanes,
(ii) coupling of reactive synthon building blocks to functional polysiloxanes; a variety of coupling strategies is presented,
(iii) the bulk properties of modified polysiloxanes by discussing the Theological properties of one polysiloxane,
(iv) gelling experiments.

(i) The Synthesis of Building Blocks

Synthesis building block 1

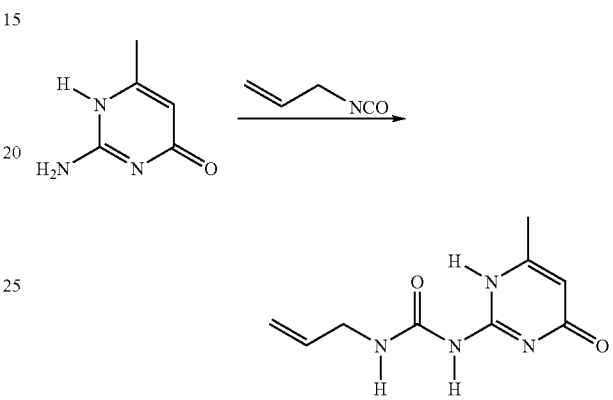

Allylisocyanate (3.12 mL) was added to methyl-isocytosine (or 2-amino4-hydroxy-6-methyl-pyrimidine, 4.0 g) suspended in methylethylketon (80 mL) and pyridine (5 mL), and subsequently stirred for 20 h at 80° C. under an argon atmosphere. After cooling to room temperature, the product was filtered, washed with pentane and dried in vacuum. A white powder was obtained. $^1$H NMR (400 MHz, CDCl$_3$): δ 13.1 (1H), 11.8 (1H), 10.4 (1H), 5.9 (1H), 5.8 (1H), 5.3 (1H), 5.2 (1H), 3.9 (2H), 2.1 (3H). FT-IR (neat): ν (cm$^{-1}$) 2948, 1703, 1666, 1582, 1521, 1256.

Synthesis building block 2

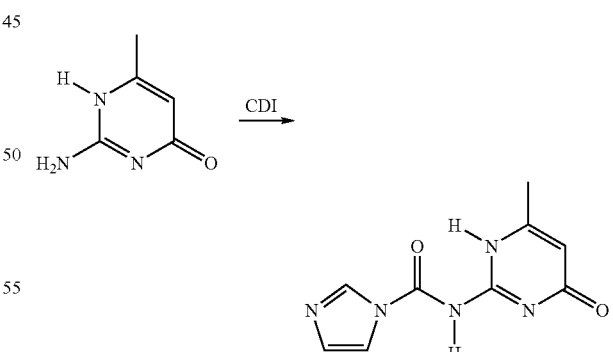

A mixture of methylisocytosine (10 g) and carbodiimidazole (20.7 g) in dried DMSO (50 mL) was heated and stirred at 100° C. under an argon atmosphere for 2 hours. The resulting solid was filtered and washed with dry acetone until a white powder remained in the filter, that subsequently was dried in vacuo and stored over P$_2$O$_5$. FT-IR (neat): ν (cm$^{-1}$) 3174, 1701, 1644, 1600, 1479, 1375, 1320, 1276.

Synthesis building block 3

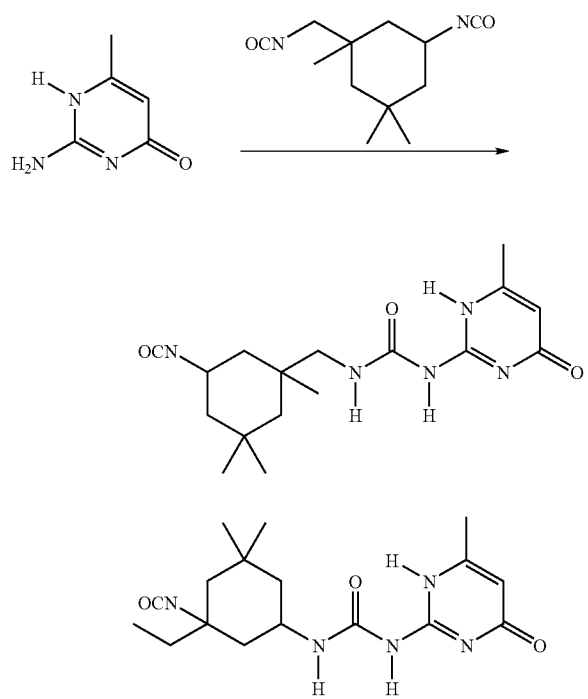

Methylisocytosine (5.2 g) was added to isophoronediisocyanate (IPDI, 50 mL) and subsequently stirred at 90° C. under an argon atmosphere for 3 days. The resulting clear solution was precipitated in heptane. The white gum was collected, heated in 150 mL heptane, cooled on ice, and filtered. The same procedure was repeated once more with the white residue, resulting in a white powder. $^1$H NMR (400 MHz, CDCl$_3$): δ 13.1 (1H), 12.0 (1H), 10.1 (1H), 5.9 (1H), 4.1-3.1 (3H), 2.1 (3H), 2.0-0.9 (15H). FT-IR (neat): ν (cm$^{-1}$) 2954, 2255, 1696, 1662, 1582, 1524, 1247.

The product exists in four different isomers: the two regioisomers depicted above in the reaction scheme are both present in cis and trans configuration. For reasons of clarity, only one isomer is depicted in the following reaction schemes, although all four isomers are present.

Synthesis building block 4

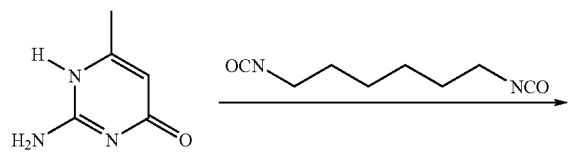

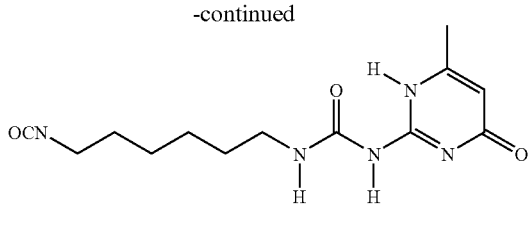

1,6-Hexyldiisocyanate (650 g) and methylisocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a liter of pentane was added to the suspension, while stirring was continued. The product was filtered, washed with several portions of pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). FT-IR (neat): ν (cm$^{-1}$) 2935, 2281, 1698, 1668, 1582, 1524, 1256.

Synthesis building block 5

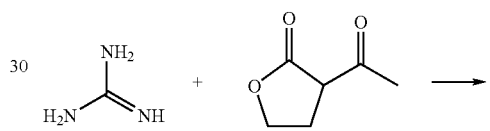

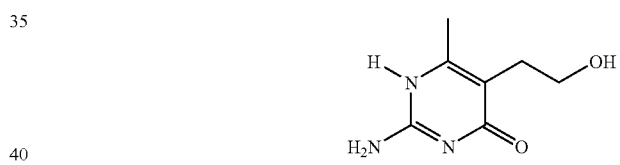

2-Acetylbutyrolactone (2 mL) and guanidine carbonate (3.3 g) were put to reflux in absolute ethanol (20 mL) in the presence of triethylamine (5.2 mL). The solution became yellow and turbid. After overnight heating at reflux, the solid was filtered, washed with ethanol, and suspended in water. The pH was adjusted to a value of ca. 6-7, and the mixture was stirred for a while. Filtration, rinsing of the residu with ethanol and drying of the solid gave the pure product. $^1$H NMR (400 MHz, DMSO-d$_6$): δ 11.2 (1H), 6.6 (2H), 4.5 (1H), 3.4 (2H), 2.5 (2H), 2.1 (3H). FT-IR (neat): ν (cm$^{-1}$) 3333, 3073, 2871, 1639, 1609, 1541, 1487, 1393, 1233, 1051, 915, 853, 789, 716.

Synthesis building block 6

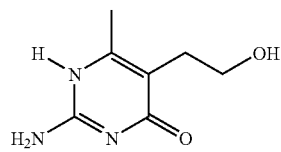 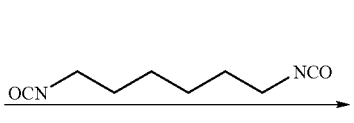

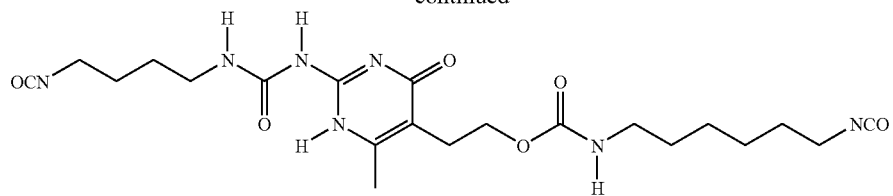

The building block 5 (1 g) was suspended in 1,6-hexyldiisocyanate (12 mL) and pyridine (1 mL) and was stirred at 90° C. A clear solution developed, and thereafter some gel particles formed (unwanted). The solution was cooled and filtered through some celite. The filtrate was dropped into pentane giving a white precipitate. This precipitate was again stirred in pentane to remove the last traces of 1,6-hexyldiisocyanate.

Isolation via filtration was followed by drying, giving the pure diisocyanate. $^1$H NMR (400 MHz, CDCl$_3$): δ 13.1 (1H), 11.9 (1H), 10.2 (1H), 4.8-4.6 (1H), 4.2 (2H), 3.3 (6H), 3.1 (2H), 2.7 (2H), 2.3 (3H), 1.7-1.2 (16H). FT-IR (neat): ν (cm$^{-1}$) 3314, 2936, 2263, 1688, 1662, 1640, 1590, 1535, 1444, 1257, 1140, 1025, 780, 742.

Building block 7

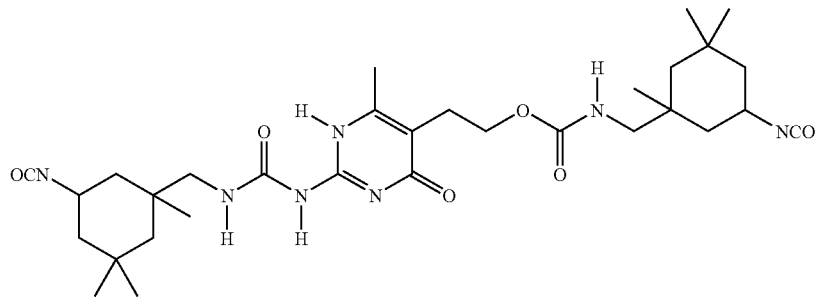

Building block 5 (12 gram) was suspended in IPDI (150 mL) and was stirred overnight at 90° C. under an argon atmosphere. A clear solution developed. The solution was cooled and precipitated in hexane. The solid was filtered, stirred in another portion of hexane, and then the product was isolated by filtration, washing with hexane and drying of the residu. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$) 2954, 2254, 1690, 1664, 1637, 1590, 1532, 1461, 1364, 1307, 1257, 1034, 791. MALDI-TOF-MS, [M$^+$]=614, [M+Na$^+$]=636. For convenience, only one isomer of the product is shown. IPDI exists in different regio- and stereoisomers, and the coupling is not selective for one of the isocyanate functions in IPDI.

(ii) Coupling of Reactive Synthon Building Blocks to Functional Polysiloxanes

Synthesis of polysiloxane 1

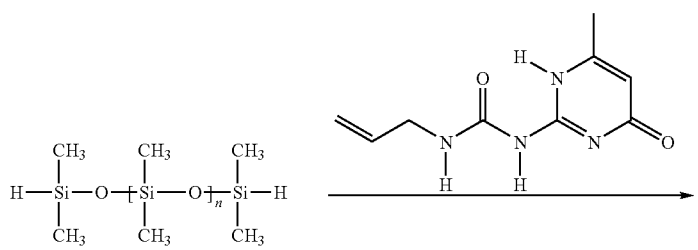

-continued

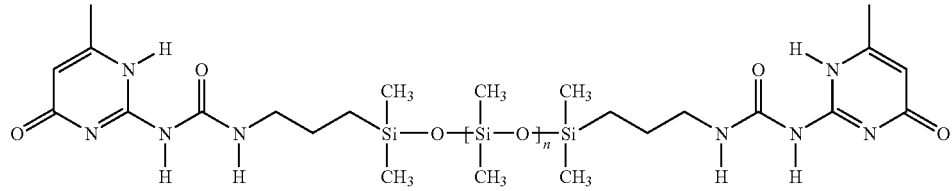

The starting dimethylhydride endblocked polysiloxane DMS H21 has a viscosity of 100 cSt and was obtained from Gelest. In a nitrogen atmosphere, a mixture of DMS H21 (10 g) and the allyl synthon building block 1 (0.8 g) was suspended in toluene (40 mL) to which a neutralized complex of platinous chloride and divinyl tetramethyl disiloxane was added in an amount sufficient to obtain a concentration of 15-20 ppm Pt-metal per total composition. This mixture was subsequently stirred at 80° C. in a nitrogen atmosphere for 16h. After cooling down, the reaction mixture was filtered and dried in vacuo. $^1$H NMR (400 MHz, CDCl$_3$): δ 13.1, 11.9, 10.2, 5.9, 3.3, 2.2, 2.0-1.5, 0.6, 0.4--0.1. FT-IR (neat): ν (cm$^{-1}$) 2963, 1701, 1670, 1587, 1527, 1258, 1010, 780.

Synthesis of polysiloxane 2

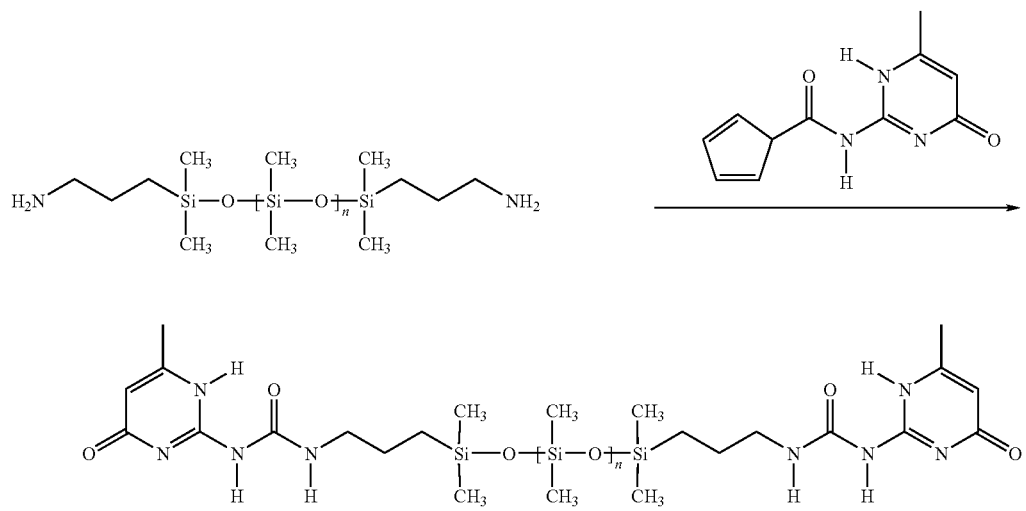

The starting bis(aminopropyl) endblocked polysiloxane DMS A21 has a viscosity of 100-120 cSt and was obtained from Gelest. The carbo-imidazole activated methyl isocytosine building block 2 (1.5 g) was added to a solution of DMS A21 (14.7 g) in tetrahydrofuran (200 mL). This mixture was subsequently heated to an oil bath temperature of 80° C. and stirred at this temperature for 16 h under an argon atmosphere. Chloroform (200 mL) was added to the reaction mixture that was subsequently filtered over silica. The clear filtrate was washed twice with saturated sodium chloride solution in water. The organic fraction was dried over Na$_2$SO$_4$, filtered and dried in vacuo to obtain an off-white, clear, elastic material. Molecular mass (M$_n$) is 3.0 kg/mol; molecular weight distribution 1.8, determined by gel permeation chromatography (polystyrene standards). $^1$H NMR (400 MHz, CDCl$_3$): δ 13.1, 11.9, 10.2, 5.9, 3.3, 2.3, 1.6, 0.6, 0.4--0.1. FT-IR (neat): ν (cm$^{-1}$) 2961, 1698, 1659, 1587, 1527, 1258, 1010, 780. SEC (THF, PS-standards): M$_w$=8.1 kD.

Synthesis of polysiloxane 3

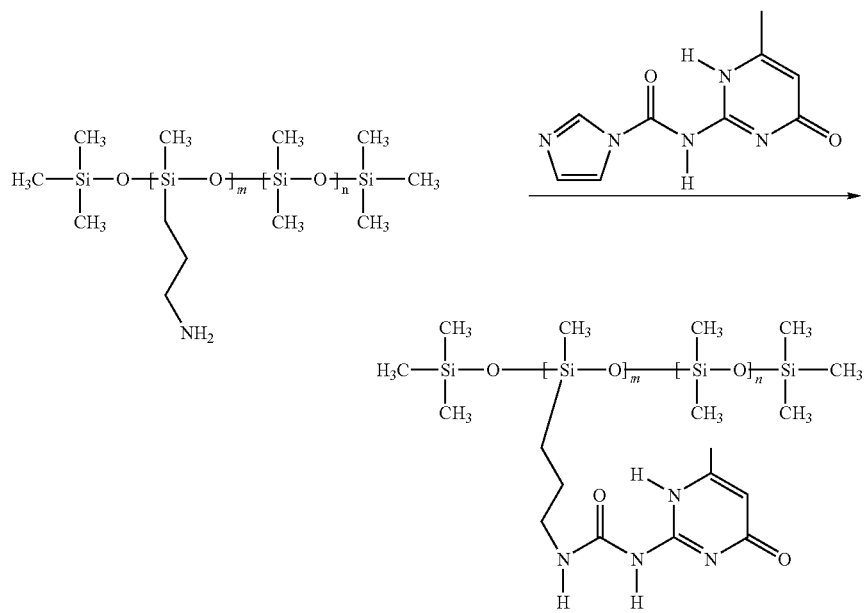

The starting aminopropyl-grafted polysiloxane AMS 152 has a viscosity of 150-260 cSt, m=4-5, and was obtained from Gelest. The carbo-imidazole activated methyl isocytosine building block 2 (2.1 g) was added to a solution of AMS 152 (15.2 g) in tetrahydrofuran (150 mL). This mixture was subsequently heated to an oil bath temperature of 80° C. and stirred at this temperature for 16 h under an argon atmosphere. After cooling, chloroform (150 mL) was added to the reaction mixture that was subsequently filtered over silica. The clear filtrate was washed twice with saturated sodium chloride solution in water. The organic fraction was dried over $Na_2SO_4$, filtered and dried in vacuo to obtain an off-white clear elastic material. Molecular mass (Mn) is 6.3 kg/mol; molecular weight distribution 1.9, determined by gel permeation chromatography (polystyrene standards). $^1H$ NMR (400 MHz, $CDCl_3$): δ 13.1, 11.9, 10.2, 5.9, 3.3, 2.3, 1.6, 0.6, 0.4--0.1. FT-IR (neat): v ($cm^-$) 2961, 1698, 1659, 1587, 1527, 1258, 1010, 780. SEC (THF, PS-standards): $M_w$=12 kD.

Synthesis of polysiloxane 4

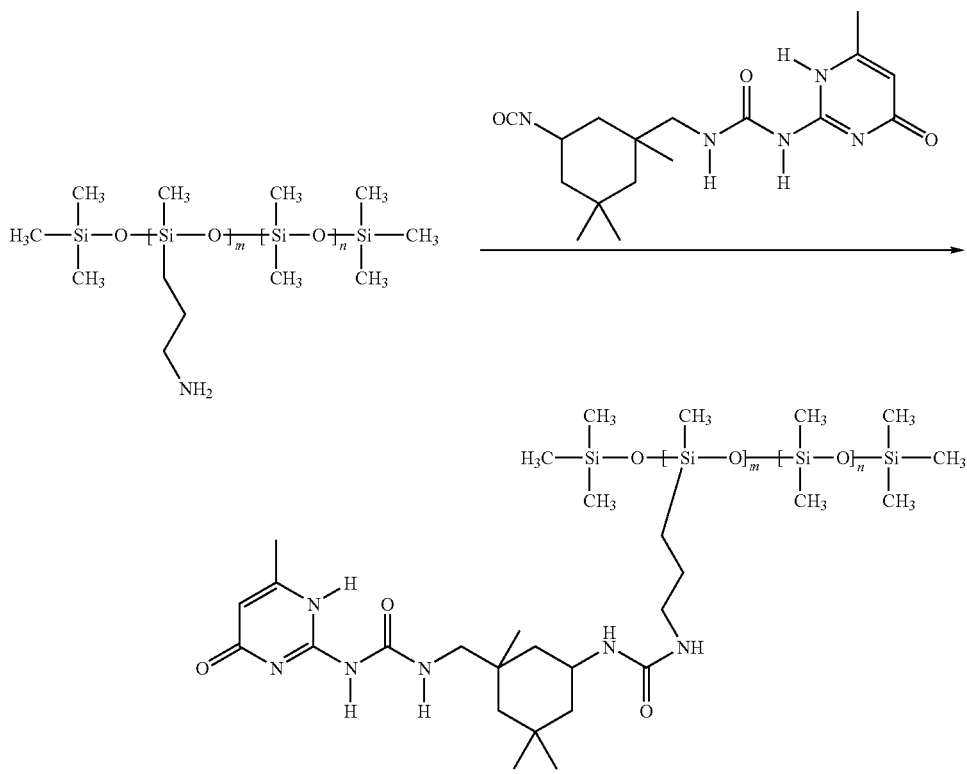

The starting aminopropyl-grafted polysiloxane AMS 162 has a viscosity of 80-120 cSt, m=3-4, and was obtained from Gelest. The isocyanate-functionalized methyl isocytosine building block 3 (2.5 g) was added to a solution of AMS 162 (15.1 g) in tetrahydrofuran (150 mL). This mixture was subsequently stirred at room temperature for 6 h under an argon atmosphere. Chloroform (100 mL) was added to the reaction mixture that was subsequently filtered over silica. The clear filtrate was dried in vacuo to obtain a clear and colorless material. $^1$H NMR (400 MHz, CDCl$_3$): δ 13.2, 11.9, 10.0, 5.9, 4.2-3.8, 3.4-2.5, 2.2, 2.0-0.8, 0.6, 0.4--0.1. FT-IR (neat): v (cm$^{-1}$) 2961, 1643, 1571, 1258, 1010, 780. SEC (THF, PS-standards): $M_w$=33 kD.

Synthesis of polysiloxane 5

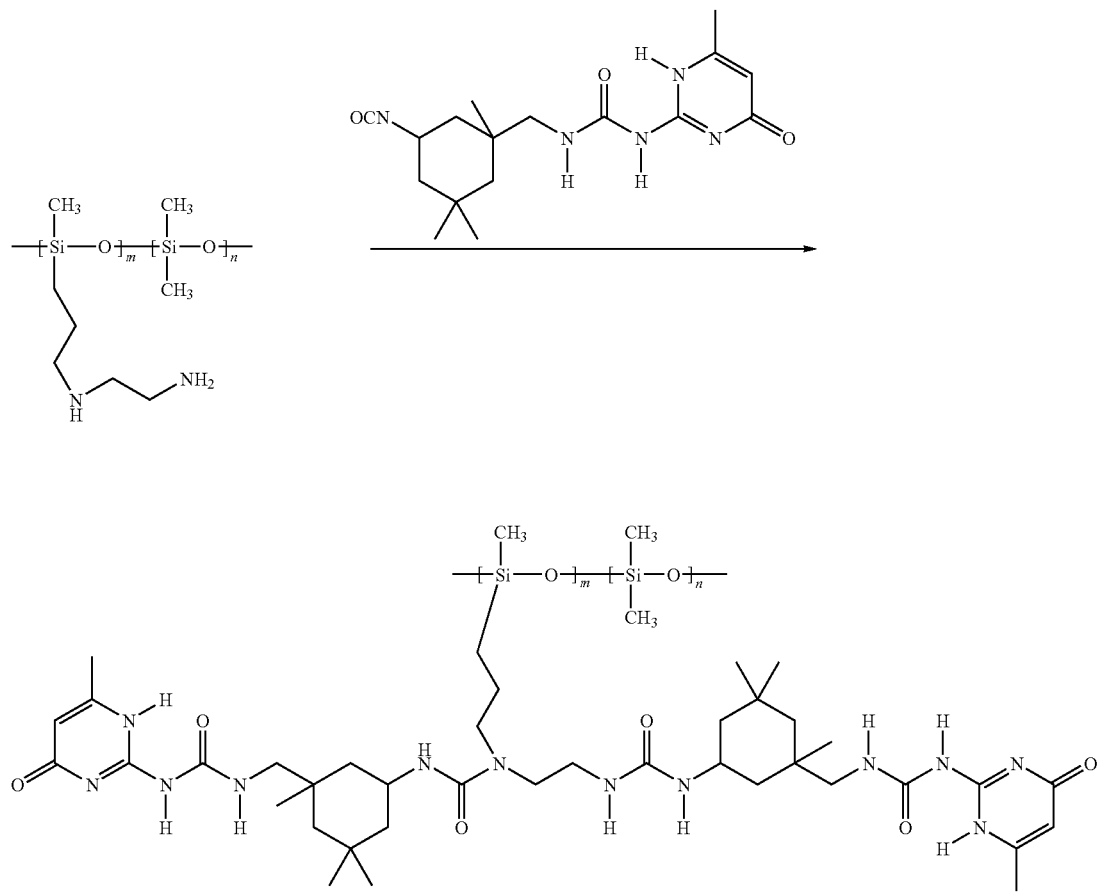

The starting aminoethylpropylamine grafted polysiloxane is also known as amidomethicone, sold for example by GE Bayer Silicones as SF1708 (viscosity=1250-2500 mm$^2$s$^{-1}$, amine equivalent is 0.8 meq/g, m and n are proprietary to GE Bayer Silicones). The isocyanate-functionalized methyl isocytosine building block 3 (5.9 g) was added to a solution of the aminoethylpropylamine-grafted polysiloxane (19.8 g) in tetrahydrofuran (500 mL). This mixture was subsequently stirred at room temperature for 2 h under an argon atmosphere. The viscous reaction mixture was diluted with ethanol (100 mL), and precipitated in methanol. The precipitate was dried in vacuo to obtain a white transparent glass. $^1$H NMR (400 MHz, DMSO/CDCl$_3$): δ 8.4-8.2, 6.1, 4.0-3.8, 3.4-2.8, 2.3, 1.8-1.4, 1.3-0.7, 0.4, 0.3--0.1. FT-IR (neat): v (cm$^{-1}$) 2962, 1663, 1614, 1573, 1258, 1010, 790. SEC (THF, PS-standards): $M_w$=28 kD.

Synthesis of polysiloxane 6

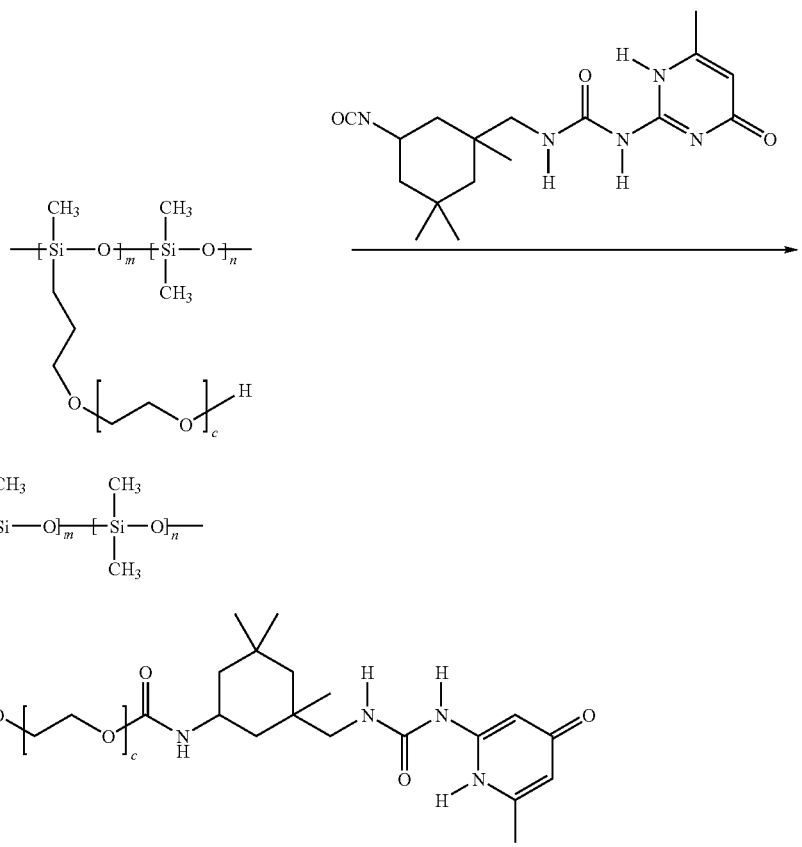

The starting oligoglycol-grafted polysiloxane is also known as dimethicone copolyol, sold for example by Dow Corning as DC193 (viscosity=465 cSt, m, n and c are proprietary to Dow Corning). The isocyanate-functionalized methyl isocytosine building block 3 (2.2 g) was added to a solution of the dried oligoglycol-grafted polysiloxane (6.13 g) in toluene (100 mL). This mixture was subsequently stirred at 80° C. for 16 h under an argon atmosphere in the presence of a few drops of dibutyltin dilaurate catalyst. The reaction mixture was concentrated to a third of its original volume, followed by precipitation in diethylether. The resulting polymer was obtained as a white gum. $^1$H NMR (400 MHz, CDCl$_3$): δ 13.1, 11.8, 10.0, 5.9, 4.2, 4.0-2.8, 2.2, 2.0-1.5, 1.4-0.7, 0.5, 0.3--0.1. FT-IR (neat): v (cm$^{-1}$) 2868, 1698, 1662, 1579, 1526, 1256, 1091, 1020, 773. SEC (THF, PS-standards): M$_w$=5.5 kD.

Synthesis of polysiloxane 7

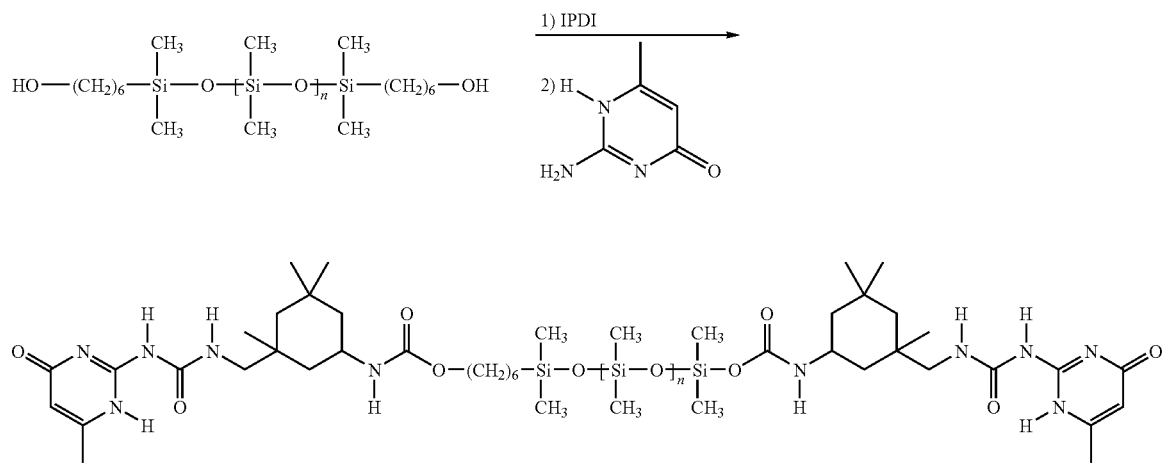

The starting bishydroxyalkyl terminated polysiloxane TEGO IS4181 has a viscosity of 60-80 MPa·s and is obtained from Goldschmidt. Polymer TEGO IS4181 (10.5 g) was dissolved in toluene (50 mL) and the resulting solution was added drop wise over a two hour period to IPDI (5.7 g) and dibutyltindilaurate (8 drops) dissolved in toluene (100 mL). The mixture was subsequently stirred at room temperature for 48 h under an argon atmosphere, followed by stirring at 40° C. for 2 h. Thereafter, pyridine (15 mL) and methylisocytosine (3.6 g) were added to this mixture, that was then boiled for 16 h. FT-IR confirmed that the NCO-groups had reacted and the volatiles were removed from the reaction mixture by evaporation. The mixture was dissolved in chloroform, the remaining solids were removed by filtration and the filtrate was added drop wise into hexanes. The polymer precipitated and was isolated as a transparent glass after drying. The molecular mass was 1.4 kg/mol; molecular weight distribution 1.3, determined by gel permeation chromatography (polystyrene standards). $^1$H NMR (400 MHz, CDCl$_3$): δ 13.1, 12.0, 10.0, 5.8, 4.5, 4.2-3.6, 3.2-2.8, 2.3, 1.8-1.5, 1.4-0.8, 0.5, 0.2--0.1. FT-IR (neat): v (cm$^{-1}$) 2958, 2924, 2852, 1694, 1663, 1613, 1574, 1526, 1462, 1257, 1018. SEC (THF, PS-standards): M$_w$=12 kD.

Synthesis of polysiloxane 8

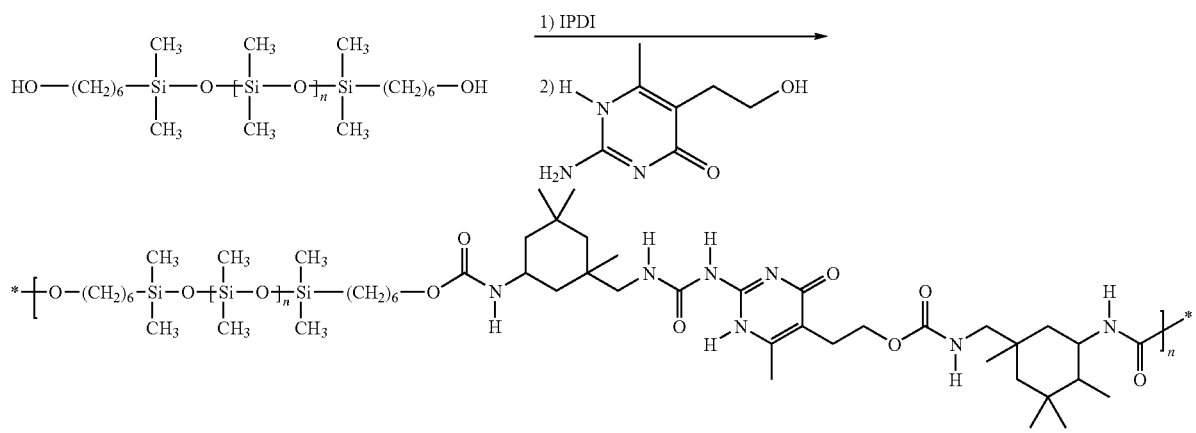

Bishydroxyalkyl terminated polysiloxane TEGO IS4181 from Goldschmidt (9.8 g) was stripped with toluene, dissolved in chloroform (20 mL) and added drop wise over a 2 hours period to a solution containing IPDI (4.75 g), chloroform (6 mL) and a few drops of dibutyltin dilaurate. The mixture was stirred overnight at room temperature. The solvent was then removed by evaporation and pyridine (40 mL) and building block 5 (1.8 g) were added. The suspension was stirred overnight at 90° C., so that a viscous clear solution was obtained. FT-IR analysis confirmed completeness of reaction as the NCO-band had disappeared. The pyridine was removed by evaporation and the polymer was dissolved in chloroform with 10% ethanol. This solution was dropped into methanol yielding precipitated polymer, that was isolated and dried in vacuo. $^1$H NMR (300 MHz, CDCl$_3$/CD$_3$OD): δ 4.8-4.5, 4.3-3.6, 3.3-2.6, 2.3, 2.0-0.8, 0.5, 0.2 -0.1. FT-IR (neat): v (cm$^{-1}$) 3238, 2958, 1714, 1661, 1635, 1580, 1536, 1437, 1257, 1019, 794. SEC (THF, PS-standards): M$_4$=7.0 kD, D=1.9.

Synthesis of polysiloxane 9

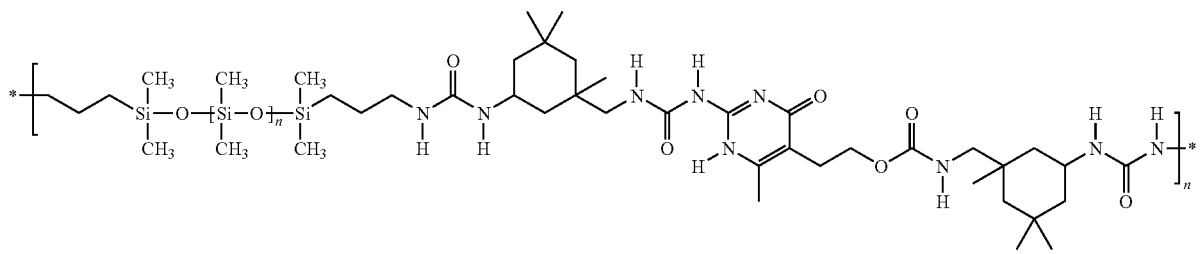

Building block 7 (1.17 g) in chloroform (100 mL) was added drop wise to bis(aminopropyl) terminated polysiloxane DMS-A32 (51.5 g; this polymer has a viscosity of 2000 cSt and is obtained from Gelest; Mn=27 kD) in chloroform (400 mL). The solution was stirred at room temperature, and after addition of the diisocyanate the mixture was heated overnight at 50° C. under an argon atmosphere. A gel had developed that was broken up by addition of 300 mL chloroform and 50 mL pyridine. The solution was stirred for another hour, the volatiles were evaporated, the mixture was co-evaporated with toluene and, finally, the product was isolated by precipitation into methanol from a dichloromethane/methanol (4/1) solution. The product was dried in vacuo. The product is a transparent, colorless, rubbery material that can be ripped upon mechanical action. $^1$H NMR (400 MHz, CDCl$_3$/CD$_3$OD): δ 4.2- 4.0, 3.8-3.6, 3.2-3.0, 2.9-2.6, 2.2, 1.7-1.5, 1.5-1.4, 1.1-0.7, 0.5, 0.3--0.5. SEC (THF, PS-standards): M$_n$=70.5 kD, D=2.7.

Synthesis of polysiloxane 10

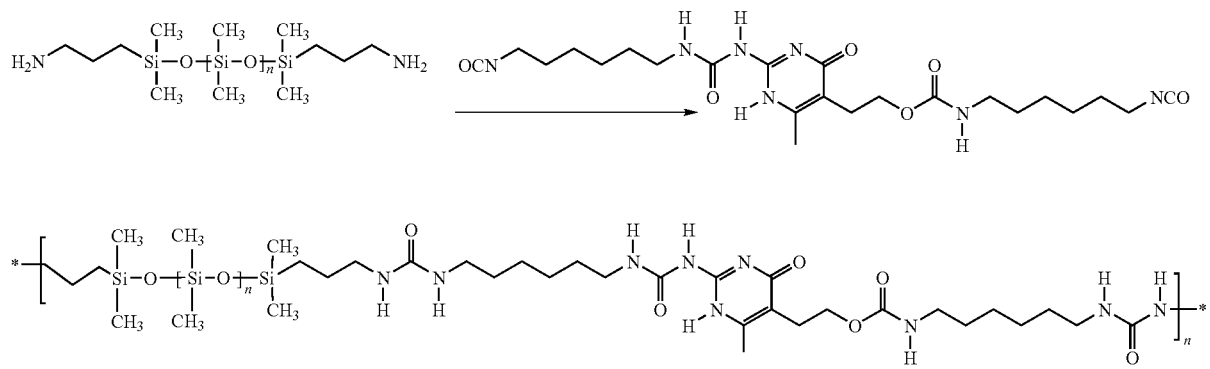

The diisocyanate building block 6 (0.126 g) in chloroform (6 mL) was added drop wise to the bis(aminopropyl) end-blocked polysiloxane DMS A32 (6.71 g; this polymer has a viscosity of 2000 cSt and is obtained from Gelest) in chloroform (20 mL). The solution was stirred at room temperature giving a viscous solution and thereafter a gel. The gel was diluted with chloroform and ethanol. Precipitation into methanol gave a polymer that was isolated and dried in vacuo. The colourless polymer has a soft touch, is somewhat elastic and crumbles upon mechanical force. 1H NMR (400 MHz, CDCl3/CD3OD): d 4.2, 3.3, 3.2, 2.8, 2.3, 1.7-1.2, 0.5, 0.3--0.1. FT-IR (neat): n (cm−1) 2963, 1725, 1695, 1665, 1607, 1582, 1447, 1413, 1258, 1079, 1009. SEC (THF, PS-standards): M$_n$=129 kD, D=1.8.

Synthesis of polysiloxane 11

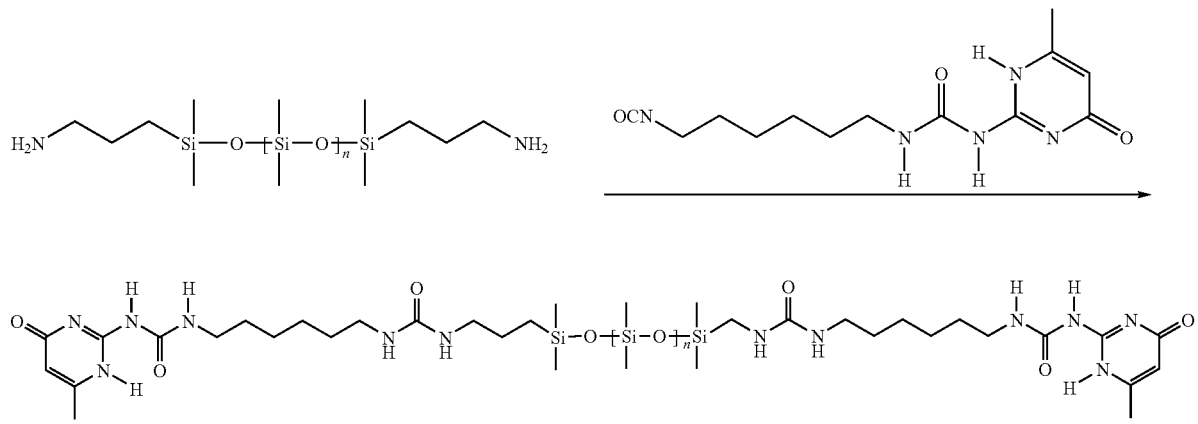

The isocyanate building block 4 (0.107 g) in chloroform (10 mL) was added drop wise to the bis(aminopropyl) end-blocked polysiloxane DMS A32 (4.93 g) in chloroform (20 mL). The solution was stirred at room temperature giving a viscous solution. After an hour, $^1$H NMR and FT-IR analysis confirmed the disappearance of both the amines and the isocyanates. The reaction mixture was dropped into methanol to give a polymer that was isolated and dried in vacuo. $^1$H NMR (400 MHz, CDCl$_3$/CD$_3$OD): δ 5.8, 3.1, 3.0, 2.2, 1.6-1.2, 0.5, 0.2--0.2. FT-IR (neat): ν (cm$^{-1}$) 2963, 1706, 1662, 1626, 1595, 1447, 1413, 1258, 1080, 1009. SEC (THF, PS-standards): M$_w$=45 kD.

Synthesis of polysiloxane 12

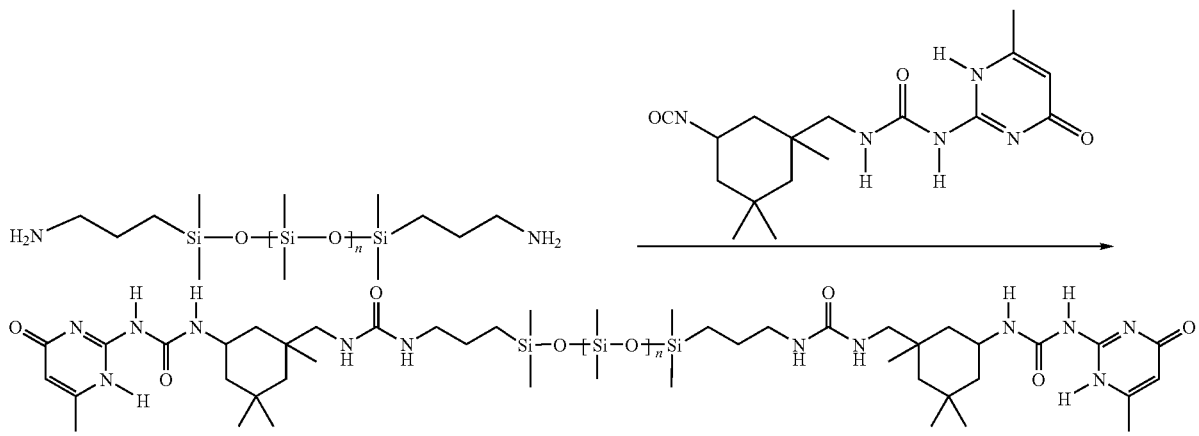

The starting bis(aminopropyl) endblocked polysiloxane DMS A21 has a viscosity of 100-120 cSt, and was obtained from Gelest. The isocyanate-functionalized methyl isocytosine building block 3 (2.1 g) was added to a solution of DMS A21 (14.3 g) in tetrahydrofuran (150 mL). This mixture was subsequently stirred at room temperature for 6 h under an argon atmosphere. Chloroform (100 mL) was added to the reaction mixture that was subsequently filtered over silica. The clear filtrate was dried in vacuo to obtain a clear and colorless material. Molecular mass is 3.3 kg/mol; molecular weight distribution 2.2, determined by gel permeation chromatography (polystyrene standards). $^1$H NMR (400 MHz, CDCl$_3$): δ 13.2, 11.9, 10.0, 6.1, 4.2-3.8, 3.4-2.8, 2.6-2.2, 2.1, 2.0-0.8, 0.6, 0.4--0.1. FT-IR (neat): ν (cm$^{-1}$) 2961, 1643, 1571, 1258, 1010, 780. SEC (THF, PS-standards): M$_w$=9.1 kD.

Synthesis of polysiloxane 13

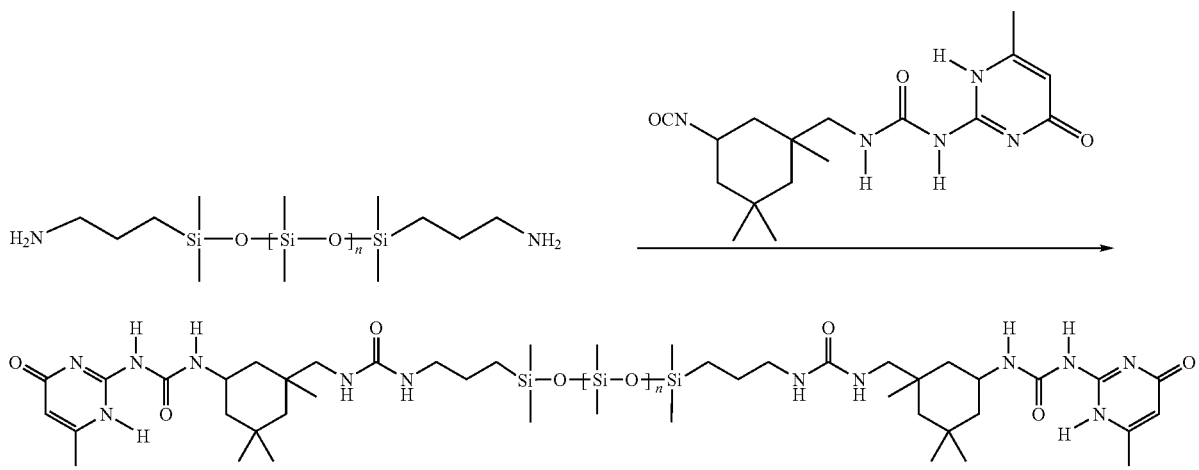

The starting bis(aminopropyl) endblocked polysiloxane DMS A32 has a viscosity of 2000 cSt, and was obtained from Gelest. The isocyanate-functionalized methyl isocytosine building block 3 (0.57 g) was added to a solution of DMS A32 (21.2 g) in tetrahydrofuran (150 mL). This mixture was subsequently stirred at room temperature for 6 h under an argon atmosphere. Chloroform (100 mL) was added to the reaction mixture that was subsequently filtered over silica. The clear filtrate was dried in vacuo to obtain a clear and colorless material. $^1$H NMR (400 MHz, CDCl$_3$): δ 13.2, 11.9, 10.0, 6.1, 4.2-3.8, 3.4-2.8, 2.6-2.2, 2.1, 2.0-0.8, 0.6, 0.4--0.1. FT-IR (neat): ν (cm$^{-1}$) 2961, 1643, 1571, 1258, 1010, 780. SEC (THF, PS-standards): M$_w$=43 kD.

Synthesis of polysiloxane 14

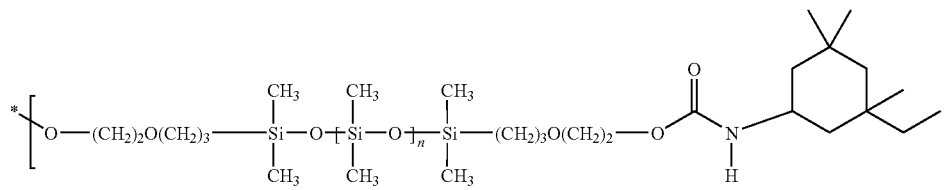

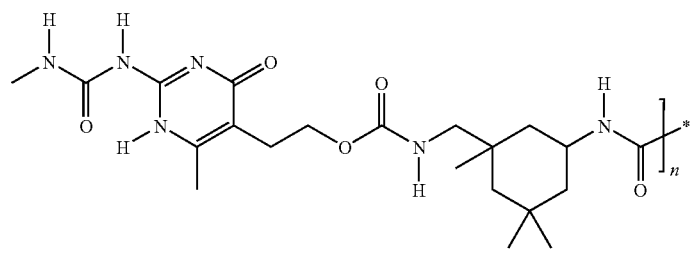

Building block 7 (0.41 g), telechelic alcohol terminated polydimethylsiloxane KF-6003 (3.53 g, Mn=5.0 kD; obtained from Shin Etsu, Japan) and a few drops of dibutyl tin dilaurate were stirred overnight in toluene (10 mL) under an argon atmosphere and at an oil bath temperature of 120° C. The polymer was isolated by precipitation into methanol, and subsequent collection and drying of the solid. The polymer is colourless, soft and transparent. $^1$H NMR (300 MHz, CDCl$_3$/CD$_3$OD): δ 4.0, 3.5, 3.3, 2.9, 2.8, 2.2, 1.5, 1.1-0.7, 0.4, 0.3--0.2. SEC (THF, PS-standards): M$_w$=66 kD, D=2.0.

Synthesis of polysiloxane 15

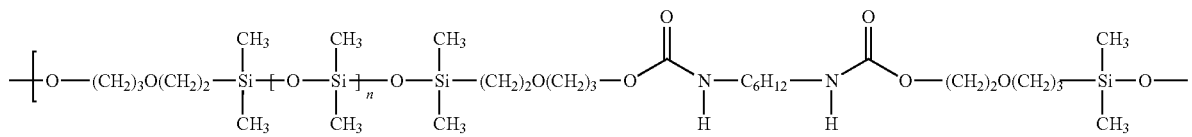

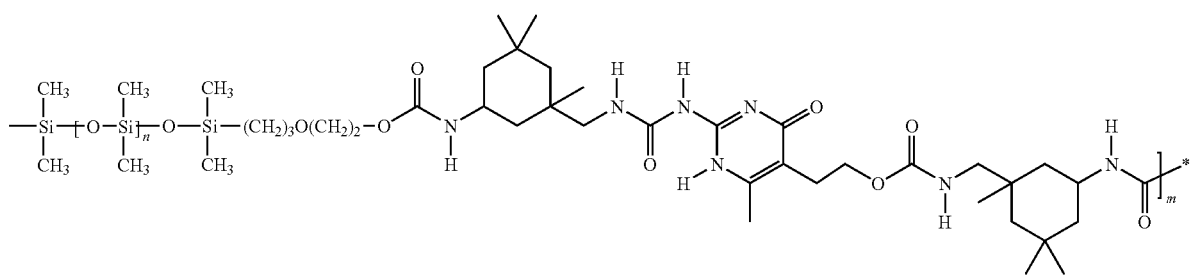

Telechelic alcohol terminated polydimethylsiloxane KF-6003 (12.14 g), 1,6-hexyldiisocyanate (0.28 g) and one drop of dibutyl tin dilaurate were stirred overnight in chloroform (35 mL) at 40° C. under an argon atmosphere. The mixture was evaporated down yielding a polysiloxane prepolymer with an average molecular weight of 15 kD. Part of this intermediate product (2.11 g), building block 7 (86 mg), one drop of dibutyltindilaurate and toluene (10 mL) was heated overnight under an argon atmosphere and at an oil bath temperature of 120° C. The polymer was isolated by precipitation into methanol, and subsequent collection and drying of the solid. The polymer is a colourless, transparent, somewhat sticky material. $^1$H NMR (400 MHz, CDCl$_3$): δ 4.8, 4.2, 3.8-3.0 (multiple signals), 2.3, 1.8-0.9 (multiple signals), 0.5, 0.2--0. SEC (THF, PS-standards): M$_n$=37 kD, D=2.8.

Synthesis of polysiloxane 16

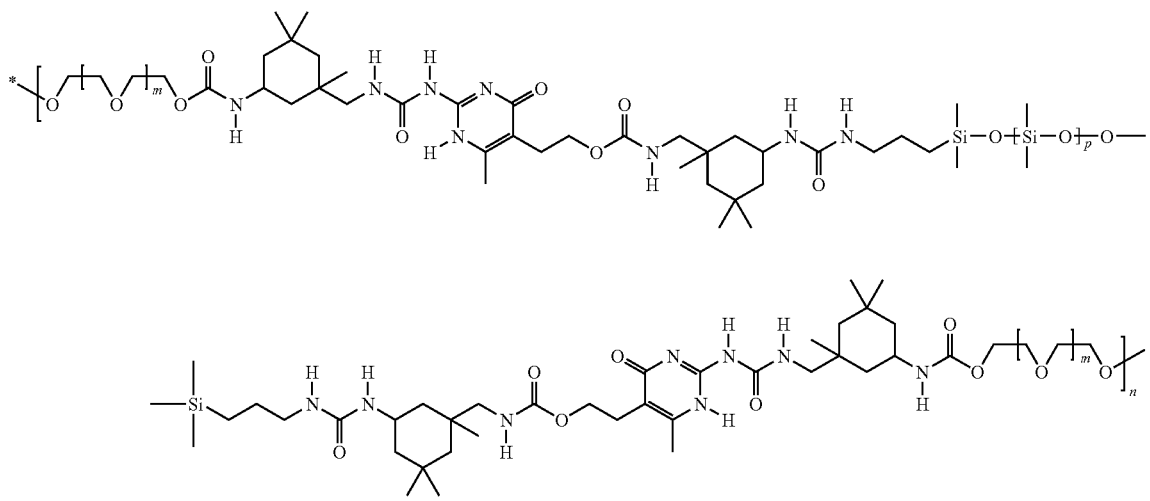

Telechelic alcohol terminated PEO-1500 (0.72 g) was stripped three times with toluene before it was mixed with building block 7 (0.59 g), two drops of dibutyl tin dilaurate and chloroform (10 mL). The solution was stirred at reflux under argon for 20 hours. Bis(aminopropyl) terminated polydimethylsiloxane DMS-A21 (2.40 g; this polymer has a viscosity of 100-120 cSt, a molecular weight of 5.0 kD and is obtained from Gelest) in toluene and a few mL of pyridine was added to the solution and stirring at an oil bath temperature of 80° C. was maintained for another 20 hours). Precipitation into water and drying gave the polymer product. The material is slightly yellow, soft and crumbles upon mechanical force. $^1$H NMR (400 MHz, CDCl$_3$/CD$_3$OD): δ 4.0, 3.6, 3.2-2.5 (multiple signals), 2.2, 1.6-0.6 (multiple signals), 0.4, 0.1--0.1. SEC (THF, PS-standards): M$_w$=10 kD.

Synthesis of polysiloxane 17

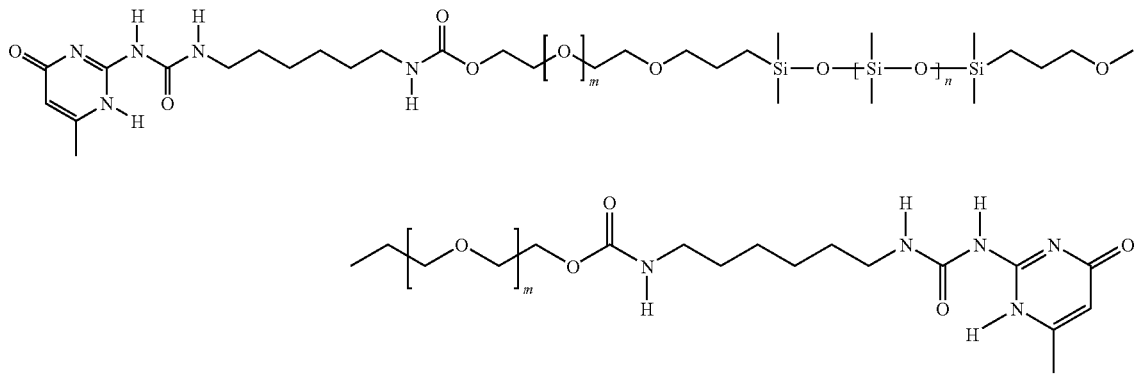

The starting hydroxy terminated poly(ethylene oxide)-polysiloxane-poly(ethylene oxide) triblock copolymer DBE C25 has a viscosity of 400-450 cSt and was obtained from Gelest. DBE C25 (30.9 g) was stripped three times with toluene before it was mixed with building block 4 (6.1 g), four drops of dibutyl tin dilaurate and chloroform (300 mL). The solution was stirred at reflux under argon for 20 hours. Subsequently, 150 mL THF was added and the viscous solution was filtered over celite, concentrated to 30% of its original volume and precipitated in hexane. The off-white material is soft and somewhat brittle. $^1$H NMR (400 MHz, CDCl$_3$): δ 13.2, 11.9, 10.2, 5.9, 4.3, 4.0-3.0, 2.3, 2.0, 1.8-1.2, 0.5, 0.4--0.1. SEC (THF, PS-standards): M$_w$=5.9 kD.

Synthesis of polysiloxane 18 solution and thereafter a gel. Heating of the oil bath to 120° C. and addition of pyridine (2 mL) gave a solution again that was stirred overnight under an argon atmosphere. Precipitation into methanol gave a polymer that was isolated and dried in vacuo. The product is a somewhat hard, transparent, colorless material that crumbles upon mechanical action. $^1$H NMR (400 MHz, CDCl$_3$/CD$_3$OD): δ 4.2-4.0, 3.8-3.6, 3.2-2.9, 2.8-2.6, 2.2, 1.7-1.5, 1.4, 1.1-0.6, 0.4, 0.2--0.2.

(iii) Bulk Properties

The polysiloxanes with supramolecular interactions between the 4H-units display unique bulk properties when considered that these polymers are essentially low in molecular weight. This is illustrated by the rheological characteristics measured for polysiloxane 4. The master curves at 40° C.

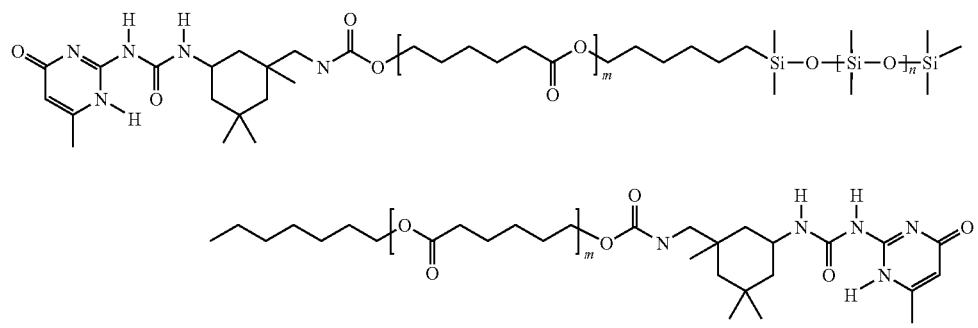

The starting hydroxy terminated polycaprolactone-polysiloxane-polycaprolactone triblock copolymer has molecular weight of 6800 and was obtained from Goldschmidt, Germany (TEGO IS 4480 P). TEGO IS 4480 P (5.8 g) was stripped three times with toluene before it was mixed with building block 3 (0.71 g), two drops of dibutyl tin dilaurate and toluene (30 mL). The solution was stirred at reflux under argon for 16 hours. Subsequently, the viscous solution was filtered over celite, concentrated to 30% of its original volume and precipitated in methanol, resulting in a white, semi-soft material. ). $^1$H NMR (400 MHz, CDCl$_3$): δ 13.1, 12.0, 10.0, 5.8, 4.6, 4.4-3.6, 3.2-2.8, 2.4-2.0, 1.8-0.8, 0.5, 0.2--0.1. SEC (THF, PS-standards): M$_w$=15 kD.

Synthesis of polysiloxane 19 of the storage (G') and loss modulus (G"), and the dynamic viscosity (η*) obtained with dynamic oscillatory shear measurements display typical viscoelastic behavior: viscous flow below 0.05 rad/s with a zero-shear viscosity of 0.9×10$^6$ Pa·s, and rubbery behavior at frequencies over 1 rad/s with a storage modulus of 1.2×10$^6$ Pa. Moreover, the complex viscosity of polysiloxane 4 decreases strongly at higher frequencies. This behavior is unique and due to the presence of the 4H-units in the polymer. In contrast, the parent non-functionalized polysiloxane shows very poor material properties: no viscoelastic transition, a viscosity that is 5 decades lower, and shift of G" of more than 4 decades towards higher frequencies.

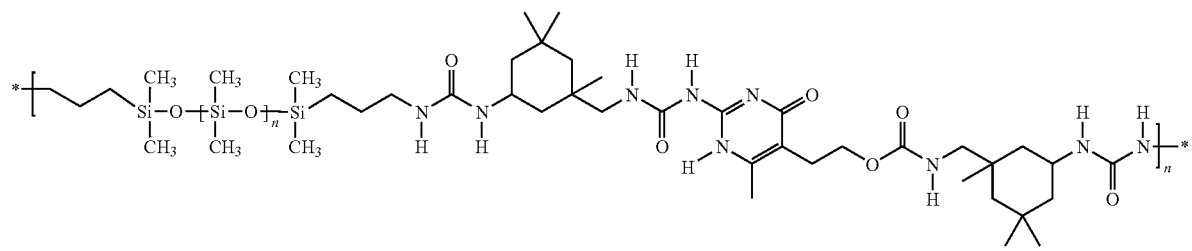

Building block 7 (0.58 g) in toluene (4 mL) was added drop wise to the bis(aminopropyl) terminated polysiloxane DMS-A21 (4.68 g; this polymer has a viscosity of 100-120 cSt and is obtained from Gelest; Mn=5 kD) in toluene (16 mL). The solution was stirred at room temperature giving a viscous (iv) Gellation Experiments Typical Procedure:

The appropriate amount of modified polysiloxane (the gellant) is added to a cyclomethicone solution followed by heating to 90° C. while mechanically stirring. When all gellant is dissolved the mechanical stirrer is removed and the mixture is cooled to room temperature, resulting in a clear gel. Table 1 lists several gels that can be obtained with the polysiloxanes disclosed in this invention.

TABLE 1

Gels obtained by mixing modified polysiloxanes with decamethylcyclopentasiloxane (D5).

| Modified Polysiloxane | weight % gellant | weight % D5 | observation |
|---|---|---|---|
| polysiloxane 3 | 20 | 80 | gel |
| polysiloxane 4 | 10 | 90 | soft gel |
| polysiloxane 4 | 12 | 88 | gel |
| polysiloxane 4 | 20 | 80 | hard gel |
| polysiloxane 10 | 2 | 98 | elastic gel |
| polysiloxane 11 | 4 | 96 | elastic gel |
| polysiloxane 12 | 5 | 95 | gel |
| polysiloxane 4/polysiloxane 12 (1/3 w/w) | 8 | 92 | gel |

Cosmetic Examples

A deodorant stick was obtained by mixing the following ingredients (amounts are given in percents by weight base on the total weight of the composition): 4% of polysiloxane 10 and 95% of decamethylcyclopentasiloxane were heated to 90° C. while stirring until a homogeneous solution was obtained. The mixture was subsequently cooled to 70° C. and 1% of a deodorant active fragrance was added as stirring was continued. The reaction was subsequently poured into the desired container and cooled down to room temperature.

An antiperspirant stick was obtained by mixing 6% of polysiloxane 13, 53% of decamethylcyclopentasiloxane, and 1% DC193 (dimethicone polyol) were heated to 90° C. while stirring until a homogeneous solution was obtained. To this mixture a heated (90° C.) solution containing 39% aluminum chlorohydrate (50% aqueous solution) and 1% DC193 was slowly added, while the mixture was vigorously stirred. Stirring was continued while the mixture was cooled to 75° C. within 15 minutes. Optionally fragrance is added, followed by pouring the hot mixture into the desired container and cooled down to room temperature.

The invention claimed is:

1. A polysiloxane having the following general formulae (3a) or (3b):

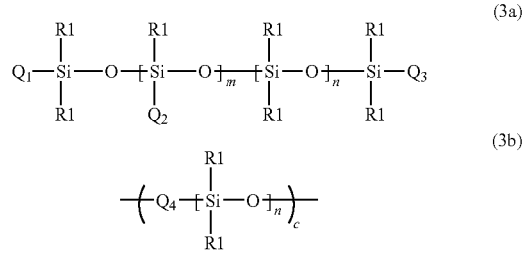

in which each R1 independently denotes a substituted or unsubstituted monovalent nonaromatic ethylenically free $C_1$-$C_{20}$ hydrocarbon radical or an aromatic radical;

(a) $Q_1$ and $Q_2$ and $Q_3$ are identical and denote one or more structural elements that are capable of forming at least four hydrogen bridges and that are attached via a linker through a silicon-carbon bond to the polymer; or (b) $Q_1$ and $Q_3$ are identical and denote one or more structural elements that are capable of forming at least four hydrogen bridges that are attached via a linker through a silicon-carbon bond to the polymer and $Q_2$ is defined as R1; or (c) $Q_1$ denotes one or more structural elements that are capable of forming at least four hydrogen bridges that are attached via a linker through a silicon-carbon bond to the polymer and $Q_2$ and $Q_3$ are defined as R1; or (d) $Q_2$ denotes one or more structural elements that are capable of forming at least four hydrogen bridges that are attached via a linker through a silicon-carbon bond to the polymer and $Q_1$ and $Q_3$ are equal and are defined as R1;

(e) $Q_4$ denotes one or more structural elements that are capable of forming at least four hydrogen bridges having two linkers that are attached through a silicon-carbon bond to the polymer chain;

wherein the one or more structural elements $Q_1$-$Q_4$ have the general formula (4) or a tautomer thereof:

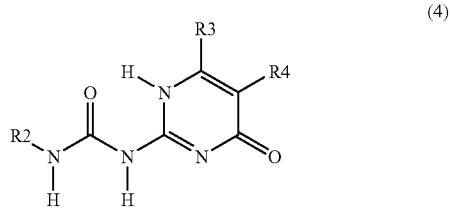

wherein either of R2, R3 or R4 denotes a linking moiety through which the structural elements $Q_1$-$Q_4$ bond to the polysiloxane, and wherein:

(i) R2 is the linking moiety and R3 and R4 are independently a hydrogen atom, alkyl or oligoethylene group; or (ii) R2 and R3 or R2 and R4 represent the linking moiety and R4 or R3, respectively, are independently a hydrogen atom, alkyl or oligoethylene group; and m, n and c are integers such that the mean molecular weight of the polysiloxane ranges from 500 to 250000 Daltons.

2. The polysiloxane according to claim 1, wherein R1 is an alkyl radical, a cycloalkyl radical, an aryl radical or an arylalkyl radical.

3. The polysiloxane according to claim 2, wherein the alkyl radical is a $C_1$-$C_{20}$ alkyl radical.

4. The polysiloxane according to claim 2, wherein the cycloalkyl radical is a $C_1$-$C_{20}$ cycloalkyl radical.

5. The polysiloxane according to claim 2, wherein the aryl radical is a $C_1$-$C_{20}$ aryl radical.

6. The polysiloxane according to claim 2, wherein the arylalkyl radical is a $C_1$-$C_{20}$ arylalkyl radical.

7. The polysiloxane according to claim 1, wherein R3 is an alkyl group or an oligoethylene group and wherein R4 is a hydrogen atom.

8. The polysiloxane according to claim 1, wherein R2 and R4 are the linking moieties and R3 is hydrogen, an alkyl group, or an oligoethylene group.

9. A thickener or gellant agent for silicone fluids comprising a polysiloxane according to claim 1.

10. A composition for personal care comprising a polysiloxane according to claim 1.

11. The composition according to claim 10, wherein the composition for personal care is cosmetic or dermatological.

12. A deodorant or antiperspirant stick comprising the composition of claim 10.

13. A silicone fluid comprising 1-40% by weight of a polysiloxane according to claim 1.

* * * * *